(12) United States Patent
Kuusela

(10) Patent No.: US 7,619,740 B2
(45) Date of Patent: Nov. 17, 2009

(54) MICROGLOSS MEASUREMENT OF PAPER AND BOARD

(75) Inventor: Reijo Kuusela, Kuopio (FI)

(73) Assignee: Honeywell International Inc., Morristown, NJ (US)

( * ) Notice: Subject to any disclaimer, the term of this patent is extended or adjusted under 35 U.S.C. 154(b) by 110 days.

(21) Appl. No.: 11/974,029

(22) Filed: Oct. 11, 2007

(65) Prior Publication Data

US 2009/0097033 A1 Apr. 16, 2009

(51) Int. Cl.
*G01N 21/47* (2006.01)
*G01N 21/55* (2006.01)

(52) U.S. Cl. .................. 356/445; 356/446; 356/601; 356/430; 356/625

(58) Field of Classification Search ......... 356/429–431, 356/71–73, 445–447, 600–601, 625; 382/108, 382/112; 250/559.04, 559.05, 559.08, 559.09, 250/341.1, 338.1
See application file for complete search history.

(56) References Cited

U.S. PATENT DOCUMENTS

| | | | |
|---|---|---|---|
| 4,750,140 A | 6/1988 | Asano et al. | |
| 4,812,665 A * | 3/1989 | Puumalainen et al. | 250/559.1 |
| 5,974,160 A * | 10/1999 | Shiratori et al. | 382/112 |
| 6,031,620 A | 2/2000 | Typpo | |
| 6,147,750 A * | 11/2000 | Johansson et al. | 356/71 |
| 6,239,436 B1 | 5/2001 | Parker et al. | |
| 6,404,502 B2 | 6/2002 | Preston et al. | |
| 6,504,617 B2 * | 1/2003 | Komulainen et al. | 356/600 |
| 6,507,403 B1 | 1/2003 | Belotserkovsky | |
| 6,842,250 B2 * | 1/2005 | Schwarz | 356/445 |
| 7,019,822 B1 * | 3/2006 | Doak et al. | 356/73 |
| 7,397,563 B2 * | 7/2008 | Kuusela | 356/430 |
| 7,460,233 B2 * | 12/2008 | Kuusela | 356/430 |
| 2005/0254068 A1 | 11/2005 | Rinn et al. | |
| 2006/0028671 A1 | 2/2006 | Katayanagi | |
| 2006/0109519 A1 | 5/2006 | Beselt et al. | |
| 2006/0256341 A1 | 11/2006 | Kuwada | |
| 2007/0103674 A1 | 5/2007 | Kuusela | |
| 2007/0103688 A1 | 5/2007 | Kuusela | |

FOREIGN PATENT DOCUMENTS

| | | |
|---|---|---|
| JP | 2006-170925 | 6/2006 |
| JP | 2006-284550 | 10/2006 |
| JP | 2007-225384 | 9/2007 |

* cited by examiner

*Primary Examiner*—Sang Nguyen
(74) *Attorney, Agent, or Firm*—Cascio Schmoyer & Zervas

(57) ABSTRACT

Microgloss is a novel two-dimensional representation of how light is reflected from a target surface area. Systems and methods for measuring the microgloss can yield data for characterizing the reflective properties of a variety of products for which surface appearance is important. These products include paper, plastics, metals, and ceramics. Microgloss characteristics can be used as parameters for controlling the supercalendering process in papermaking. Microgloss characteristics can be used in conjunction with standard gloss to classify products.

17 Claims, 3 Drawing Sheets

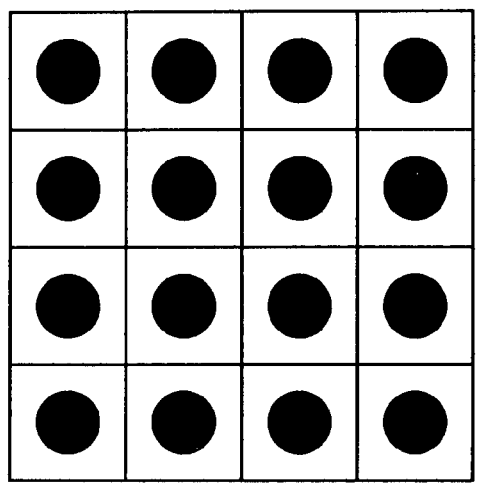
FIG. 2A
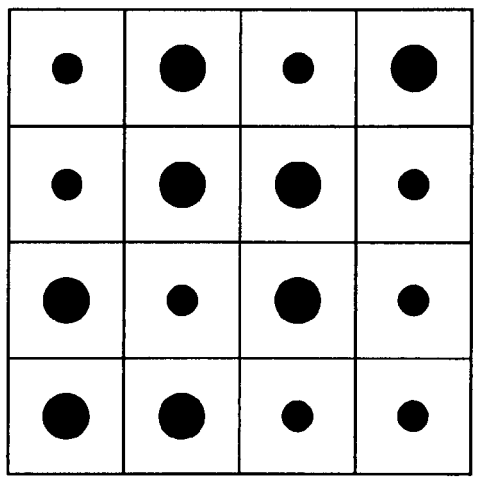     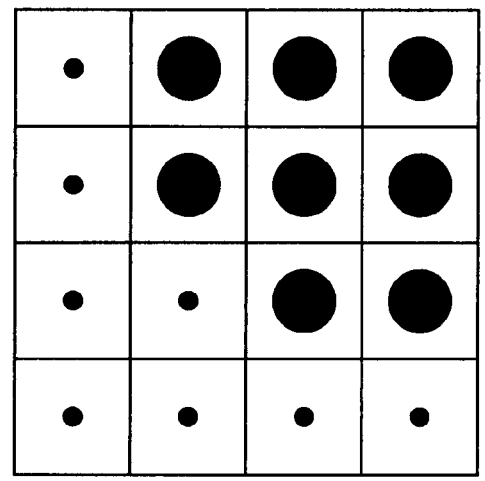
FIG. 2B              FIG. 2C

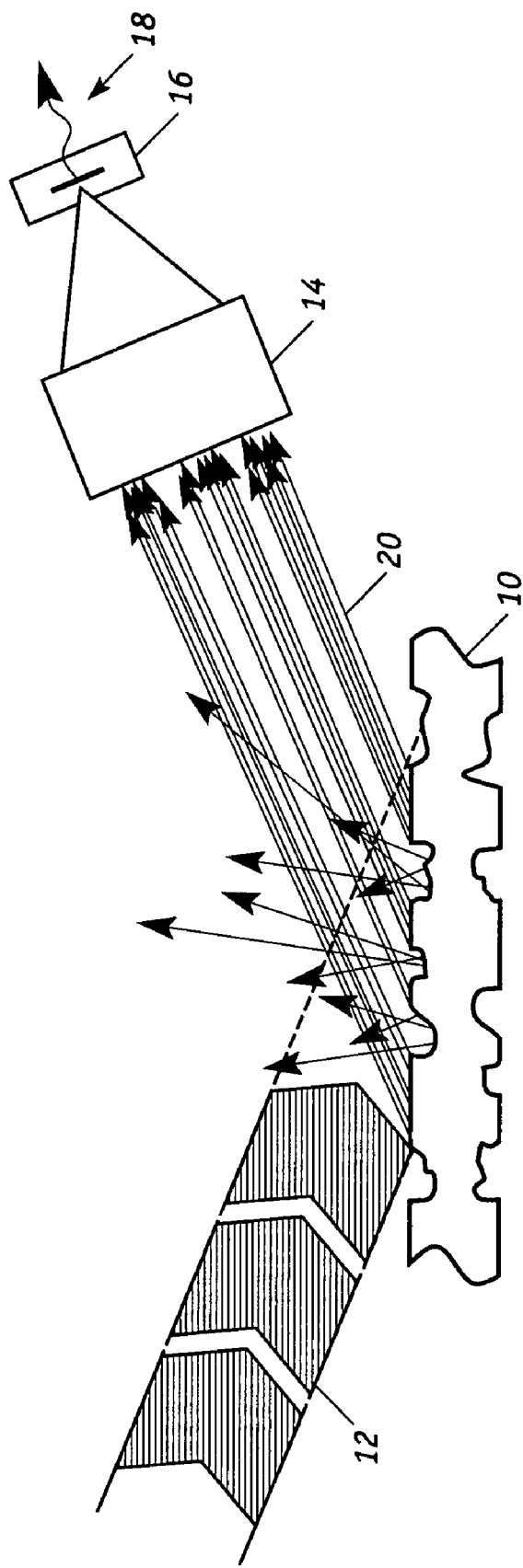
FIG. 3 *(Prior Art)*

MICROGLOSS MEASUREMENT OF PAPER AND BOARD

FIELD OF THE INVENTION

The present invention relates generally to techniques for detecting microgloss, which is a two-dimensional representation of how light is reflected from a target surface area, and more particularly to the generation of microlevel images and the calculation of microgloss grades or values for paper, painted or coated articles, and other products for which visual appearance is important. Microlevel images are two-dimensional light intensity distribution profiles of a surface and are derived from light that is reflected from a target area on the surface being inspected. The target area is illuminated with light that is directed thereto at a predetermined angle of incidence and the light that is detected is that which is reflected at an angle that is the same as the angle of incidence. The microlevel images can be employed to derive novel parameters for characterizing the reflective properties for a variety of products.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The papermaking machine is, in essence, a water removal system. After being dried, the paper is run between drums that impart the desired smoothness. This process is referred to as calendering and the more times paper is calendered the smoother the finish of the paper becomes. To create glossy paper, uncoated paper may be coated with a paint-like product and buffed by rollers under very high pressure, to create a shiny appearance. This process is referred to as supercalendering. Additional varnish layers may be applied to paper during the printing process to provide a gloss surface on the paper.

Supercalendering processes can either be an on-machine continuous process or an off-machine batch process. It is used to improve the paper sheet's surface properties, such as smoothness and gloss (shininess), which are critical for high-quality printing paper. Like other papermaking machine cross direction processes, the supercalendering process is a two-dimensional (spatial and temporal) process. The process starts with unwinding the paper sheet from the reel at an unwinder. The paper sheet is then fed between a series of rolls that are arranged in a vertical stack. The rolls are typically arranged to alternate hard and soft with two consecutive soft rolls in the middle of the stack. The paper sheet passes out from the bottom of the stack and wound up on a reel.

In paper production various grades of paper having different surface gloss are produced to suit various applications. During paper production, it is desirable to periodically or continuously measure the gloss of the surface of the paper to ensure that the paper surface has the desired gloss. This is typically done immediately after supercalendering with a gloss sensor that can be scanned back and forth along the cross direction of the moving sheet.

Two gloss sensor standards have been developed in the paper industry. The first standard, outlined under DIN 54502, for regular gloss measurements specifies that the measurements are to be taken using an angle of 75° for the incident light beam from a line perpendicular to the measured surface. For high-gloss measurements, measurements are taken using an angle of 45° for the incident light beam from a line perpendicular to the surface to be measured. If measurements at both angles are to be made, two separate and distinct sensors are generally used. The second standard, outlined under TAPPI T480, specifies that the measurement is to be taken only using an angle of 75° for an incident light beam from a line perpendicular to the measured surface.

Conventional devices, for measuring the gloss of paper surfaces, utilize an optical system that measures the intensity of a beam of light reflected from the paper surface. Gloss sensors are described in U.S. Pat. No. 6,404,502 to Preston et al. and U.S. Pat. No. 6,507,403 to Belotserkovsky. Typically, the gloss of the paper surface is determined by comparing its reflectance to the reflectance of a known gloss standard, such as a glass tile having a polished surface with a known gloss. Alternatively, the average intensity of the pixels can be employed. Additional techniques for measuring gloss numbers are described in US Patent Application Numbers 2007/0103674 and 2007/0103688 both to Kuusela.

As illustrated in FIG. 3, in measuring the reflectance of the paper surface 10, light 12 of known intensity is projected onto the surface, and a sensor which is responsive to the intensity of light is positioned to measure the intensity of the reflected light 20 from the paper surface. The sensor includes a condensing optics 14 and a single photometric detector 16 that yields signals 18 that represent a single intensity value 18. The gloss level is calculated as the ratio of the reflecting light beam intensity to the intensity of the illuminating light beam. As is apparent, this method yields only one average gloss value for the illuminated area of the paper. Most products such as paper, board, painted surfaces, etc. exhibit microlevel gloss variations within the illuminated area which cannot be measured by prior art techniques. Because of this "internal" gloss variation, products with the same conventional gloss value can manifest different visual outlooks to a consumer. The art is in need of a gloss sensor that is capable of distinguishing micro-level differences in the gloss on the surfaces of paper and other products.

SUMMARY OF THE INVENTION

The present invention is based in part on the recognition that analysis of microlevel images that are the two-dimensional light intensity distribution profiles or patterns that are derived from illuminating light that is reflected from product surfaces can yield valuable information concerning the quality of numerous products. In particular, the product's microgloss is determined by comparing the microlevel image's two-dimensional light intensity distribution profile to the intensity of the uniform profile of the illumination light. The microgloss is in essence a two-dimensional representation of how light is reflected over a target surface area.

In one aspect, the invention is directed to a method of classifying a reflective characteristic of a product that includes of the steps of:

illuminating a target area on a surface of the product with a beam of light of known intensity incident to the target area at a predetermined angle of incidence;

detecting light, that is reflected from the target area at an angle of reflection that is the same as the angle of incidence; and generating a two-dimensional distribution profile of the light that is reflected from the target area; and calculating a microgloss value for the target area.

In another aspect, the invention is directed to a sensor for optically measuring surface characteristics that includes:

a source of light that directs an illuminating beam of light of known intensity incident to a target area on the surface at a predetermined angle of incidence;

a detector;

imaging optics which is configured to collect light, that is reflected from the target area at an angle of reflection that is the same as the angle of incidence, to the detector which generates signals that represent a two-dimensional distribution profile of the light that is reflected from the target area surface is generated.

In a further aspect, the invention is directed to a method for detecting surface characteristics of a sample surface that includes the steps of:

illuminating a target area on the surface with a beam of light of known intensity incident to the target area at a predetermined angle of incidence;

detecting light, that is reflected from the target area at an angle of reflection that is the same as the angle of incidence; and generating a two-dimensional distribution profile of the light that is reflected from the target area.

The inventive technique can be employed to determine the microgloss value of any surface especially of finished products where their aesthetic appearances are important. The microgloss value is particularly useful when used in conjunction with the conventional gloss value of products such as plastics, metals, ceramics, and paper and paper products, e.g., board. Other important products include coated or painted articles such as automobile parts. With respect to paper, the microgloss value is also a useful criterion to the printability of high quality paper. While the invention will be illustrated in measuring the microgloss and related properties of paper, it is understood that the invention can be employed to analyze the surface characteristics of a variety of other products as well.

BRIEF DESCRIPTION OF THE DRAWINGS

FIGS. 2A-2C depict representative microlevel images that are generated by the microgloss measurement sensor; and FIG. 3 shows a prior art gloss detector.

DESCRIPTION PREFERRED EMBODIMENTS

Figure 1:
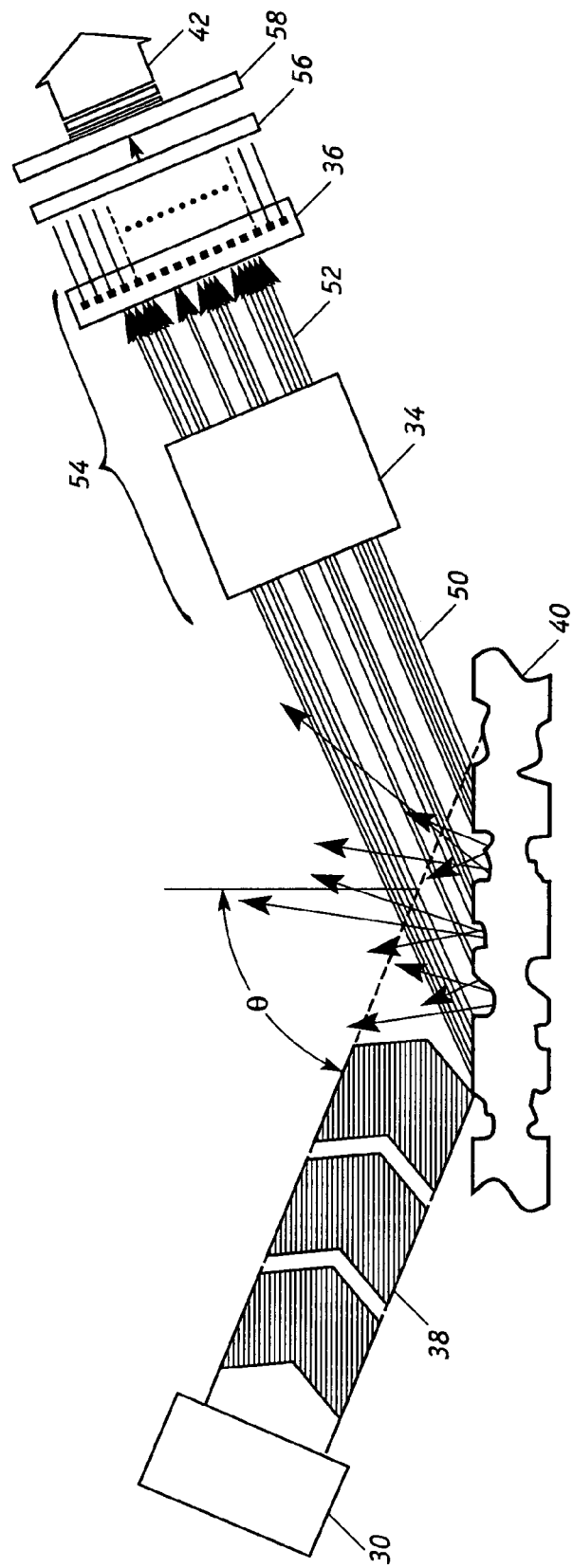
FIG. 1 shows an embodiment of the microgloss measurement sensor.

FIG. 1 shows an embodiment of the inventive microgloss device for measuring surface characteristics of paper 40 that, in this example, has a rough surface. The device employs a source of illuminating light 30 and an image detector 54 that typically includes an imaging optics 34 and detector matrix 36. In operation, a light beam 38 from source 30 is directed toward paper 40 to illuminate an image or target area on its surface. The light beam is directed at a predetermined angle of incidence θ and the imaging optics 34 collects reflected light 50, which includes essentially only light that is reflected at an angle of reflection that is the same as the angle of incidence. The focused light 52 is directed into the detector matrix 36. As is apparent, incident light that is reflected from the smooth surface (as specular reflection) within the target area is captured by the imaging optics 34 whereas incident light is scattered from the rough surface within the target area (as diffuse reflection) and is not captured by the imaging optics 34. In practice some light is also absorbed by the paper 40. The output from the detector matrix 36, which are electrical signals representing an image of the surface, can be converted with an image processor 56 into surface patterns that can be observed visually. Finally, a pattern recognition device 58 can also be employed to compare the surface patterns with predetermined reference patterns in order to automatically assign a microgloss grade or value 42 for that product. The device 58 can also include a microprocessor and software to perform statistical analysis of the patterns. The surface patterns can be analyzed by various techniques as described herein.

When the paper 40 is stationary, the microgloss measuring device yields a single image and/or value of the static target area; however, when the paper 40 is part of a continuous moving sheet, the microgloss measuring device can function as a continuous monitoring or inspection apparatus that generates a series of real time data which can be used for process control of the papermaking machine. For example, a microgloss measuring device can be mounted on a rail to take measurements of paper exiting the supercalendering step. This device will yield fixed-point readings along the machine direction (MD) of the paper that is produced. Alternatively, multiple devices can be mounted along the cross direction (CD) of the moving paper so that both MD and CD readings are obtained. On-line measurements can also be generated by mounting an on-line device that scans over the moving sheet of paper in the cross direction. Suitable scanning mechanisms are described in US Patent Application Publication No. 2006/0109519 to Beselt et al.

The light source 30 preferably provides high uniform intensity illumination that consists of a constant stream of energy within a wavelength required for measurement. For paper products, suitable resolution can be achieved with visible light preferably with the intensity maximum at the green light region. Infrared radiation (IR) can also be used in certain applications although in practice the limited wavelength regions in commercial detector matrices restrict the feasibility of using IR. The light source 30 can be amplitude modulated by conventional mechanical devices such as choppers, shutters, tuning forks and the like to enhance the signal-to-noise ratio. Another exemplary modulating technique employs electro-optical shutters such as Kerr cells and Pockels cells that are positioned in the light beam path of the light source and acousto-optical devices such as acousto-optical tunable filters. Alternatively, direct modulation of a drive current that is coupled to the light source to generate pulsed illumination can be used.

Preferred light source devices include light-emitting diode (LED), laser diode, or an array of LEDs or laser diodes. When the light source is modulated to create a stroboscopic flash effect, for instance, a high modulation rate is preferred. The resulting short exposure times allow the detector matrix 36, with correspondingly short integration times, to obtain better images of the target area by reducing or eliminating the adverse effects caused by motion-blurring in the direction of movement of the paper 40. In the case where the detector matrix is a charge-coupled device (CCD), a short integration time allows the pixels to collect less light and a longer integration time lets pixels collect more light. Alternatively, or in addition to modulating the light source, the detector matrix 36, e.g., CCD camera, that operates at a high exposure rates, i.e., short integration times, can be selected. In this case, the illumination can be continuous which makes it is easier to maintain consistent illumination at different measurements.

As shown in FIG. 1, the imaging optics 34 is configured to collect light beam 50 that is reflected from the target area at the predetermined angle of reflection. Suitable imaging optics 34 can be constructed of conventional lens. The angles of incidence and reflection are measured relative to an axis or line that is perpendicular to the plane of paper 40.

The angle of illumination e highly influences the amount of light that reflects from a product's surface. While the microgloss sensor can be configured to take measurements at any angle between 0 and 90°, the angle of illumination will typical range from about 10° to 80° depending on the product. For high gloss materials, the angle will be typically be lower than that for lower gloss materials. As described further herein, the microgloss sensor can also be used to measure the standard gloss value of a material, which corresponds to the ratio of the reflected light beam intensity to the illuminating light beam intensity. Within the paper industry, the gloss is measured at 45° or 75° according to DIN or TAPPI standards. By using the inventive microgloss sensor for a paper product, for example, the sensor not only provides the microgloss grade or value, it also computes the gloss value. In this fashion, a paper product will have dual classifications: (i) gloss and (ii) microgloss.

The shape and size of the illuminated target area will depend on the product being measured. The target area preferably is at least about 25 mm² and is typically from 100 mm² to 1000 mm² in size. As is apparent, the larger image area, the more representative is the microgloss values that are determined. For measuring paper, the shape of the target area can be a square or ellipse, for example. With the microgloss sensor, it is expected that better than 100 μm resolution of the details on the target surface can be achieved.

The image detector matrix 36 is a two-dimensional image sensor for detecting the light intensity pattern that is reflected from the surface of the product being inspected. The image sensor comprises a large number of light-receiving elements or pixels and the image is formed on the basis of outputs from each pixel. The image detector matrix is preferably a charge-coupled device (CCD) or complementary metal oxide semiconductor (CMOS) camera that is equipped with appropriate imaging optics 34, e.g., lenses, to focus light that is reflected from the image area into the camera. A video camera can also be used for continuous detection.

FIGS. 2A, 2B and 2C are idealized two-dimensional images for three different hypothetical target areas on paper. Each image depicts a collection of outputs, whose relative individual intensity is denoted by the diameter of the solid circle, which are generated by the detector matrix pixels of the microgloss sensor. While these microlevel images are represented as 4×4 matrices, an actual detector matrix will have a much higher number of pixels. Based on the output pattern of FIG. 2A, this two-dimensional image indicates that the corresponding target area is very smooth as each pixel captured the same amount of reflected light as each pixel output is the same size. The two-dimensional image of FIG. 2B corresponds to target area with less uniformity. Finally, the two-dimensional image FIG. 2C corresponds to a target area in which approximately half of the target area is quite smooth and the other half being rougher; however, given that the smaller outputs are of the same intensity, the rougher surface exhibits a consistent irregularity.

Microlevel images can be converted into visible images for visual observation, but analysis by an individual is highly subjective. A more practical application is to use conventional pattern recognition software to compare the microlevel images to reference images of known profiles and to assign a microgloss grade or value to each microlevel image. For example, the microlevel image as depicted in FIG. 2A can be assigned a microgloss grade of 100 in a scale of 0 to 100 where 100 is for a microlevel image where the two-dimensional light intensity distribution profile shows complete balance. By knowing the microgloss grade or value for a particular product, one can better evaluate the more subtle aesthetic features which otherwise cannot be gauged by determining the conventional gloss value alone.

The microlevel images can also be analyzed to generate an average or normal gloss value. This is obtained by calculating the ratio of the intensity of the incident light to the intensity of the reflected light for each pixel of the microlevel image. The average gloss value would be the average of all the individual ratios.

It should be noted that the microlevel images can also be used to determine the conventional gloss value which is calculated by simply aggregating the intensities of all the pixels of the detector matrix and obtaining a ratio of this aggregate intensity to the illumination intensity.

The microlevel images can be subject to statistical analysis to extract information that is used to control the supercalendering process in order to produce products with the desired microgloss values. In addition, novel parameters, such as the microgloss value described above, can be developed to classify paper and other products under a system whereby one or more subtle visual features of the product can be distinguished and quantified. These new classification systems can augment the current gloss system that is based on standard gloss measurements For instance, the absolute maximum (max) and minimum (max) values of the image profiles can be measured and thereafter their (i) difference: max−min and (ii) relative difference: ((max−min)/(average microgloss))×100%, can be both be derived. Similar calculations can be made when the steepness or rate of microgloss change for various profiles are ascertained from derivatives of the profiles. The mean, standard deviation (both MD and CD), variance, and other measures of how microlevel images are distributed can be readily derived by applying conventional statistical methods. In this regard, another useful novel parameter which is referred as the "glitter" or "sparkling" value or number is defined as: (standard deviation of microgloss)/(average microgloss))× 100%.

Finally, once a desired minimum standard of the two-dimensional image profile, as represented by a minimum microgloss value, for a particular grade of paper is established, the inventive microgloss measurement device can be employed as part of a scanning sensor, for example, to determine if paper being produced deviates from the norm and to what extent. Data from the microgloss measurement device can be analyzed to generate, for example, a map of the paper showing a two-dimensional distribution of the microgloss values. From this map, one can readily determine the location and number of target areas where the microgloss values are below the norm, above the norm, and comparable to the norm. In addition, the size, the shape, the orientation, and number of these areas can also be determined.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A sensor for optically measuring surface characteristics of a product that comprises:
   a source of light that directs an illuminating beam of light of known intensity incident to a target area on the surface at a predetermined angle of incidence θ as measured relative to an axis or line that is perpendicular to a plane of the product and wherein the target area is coplanar with the plane of the product;

a detector;

imaging optics which is configured to collect light, that is reflected from the target area at an angle of reflection that is the same as the angle of incidence θ, to the detector which generates signals that represent a two-dimensional distribution profile or the light that is reflected from the target area surface is generated, and means for calculating a microgloss value for the target area based on the signals that represent the two-dimensional distribution profile, wherein the means for calculating the microgloss value for the target area comprises a pattern recognition device that compares the signals that represent the two-distributional distribution profile to predetermined reference patterns and that assigns the microgloss value.

2. The sensor of claim 1 further comprising means for calculating a gloss value for the target area.

3. The sensor of claim 1 further comprising means for statistically analyzing the two-dimensional distribution profile.

4. The sensor of claim 1 wherein the detector comprises a CCD or CMOS camera.

5. The sensor of claim 1 wherein the angle of incidence ranges from 10 to 80 degrees as measured from an axis that is perpendicular to the surface.

6. The sensor of claim 1 wherein the source of light directs a beam of visible light with the intensity maximum at the green light region.

7. A method for detecting surface characteristics of a sample surface that comprises the steps of:

illuminating a target area on the surface with a beam of light of known intensity incident to the target are at a predetermined angle of incidence θ as measured relative to an axis or line that is perpendicular to a plane of the sample and wherein the target coplanar with the plane of the sample;

detecting light, that is reflected from the target area at an angle of reflection that is the same as the angle of incidence θ;

generating a two-dimensional distribution profile of the light that is reflected from the target area; and calculating a microgloss value for the target area based on the two-dimensional profile of light that is reflected from the target area, wherein the step of calculating the microgloss value for the target area comprises comparing the two-dimensional distribution of light to predetermined reference patterns and assigning the micogloss value.

8. The method of claim 7 further comprising the step of calculating a gloss value for the target area.

9. The method of claim 7 further comprising the step of statistically analyzing the two-dimensional distribution profile.

10. The method of claim 7 wherein the detector comprises a CCD or CMOS camera.

11. The method of claim 7 wherein the angle of incidence ranges from 10 to 80 degrees as measured from an axis that is perpendicular to the surface.

12. The method of claim 7 wherein the surface is that of a paper product.

13. A method of classifying a reflective characteristic of a stationary paper product that comprises of the steps of:

illuminating a static target area on a surface of the station paper product with a beam of light of known intensity incident to the static target area at a predetermined angle of incidence θ as measured relative to an axis or line that is perpendicular to a plane of the stationary paper product and wherein the static target area is coplanar with the plane of the stationary paper product;

detecting light, that is reflected from the target area at an angle of reflection that is the same as the angle of incidence θ;

generating a two-dimensional distribution profile of the light that is reflected from the static target area; and calculating a microgloss value for the static target area based the two-dimensional distribution profile, wherein the step of calculating the microgloss value for the static target area comprises comparing the two-dimensional distribution of light to predetermined reference patterns and assigning the micogloss value.

14. The method of claim 13 further comprising the step of calculating a gloss value for the static target area.

15. The method of claim 13 wherein the detector comprises a CCD or CMOS camera.

16. The method of claim 13 wherein the angle of incidence ranges from 10 to 80 degrees as measured from an axis that is perpendicular to the surface.

17. The method of claim 13 wherein the static target area is from 100 mm$^2$ to 1000 mm$^2$ in size.

* * * * *

UNITED STATES PATENT AND TRADEMARK OFFICE
CERTIFICATE OF CORRECTION

PATENT NO. : 7,619,740 B2
APPLICATION NO. : 11/974029
DATED : November 17, 2009
INVENTOR(S) : Reijo Kuusela It is certified that error appears in the above-identified patent and that said Letters Patent is hereby corrected as shown below:

Column 7, Claim 1, line 9, "or" should be --of--.
Column 7, Claim 7, line 35, "are" should be --area--.
Column 7, Claim 7, line 38, "target coplanar" should be --target area is coplanar--.
Column 8, Claim 13, line 19, "station" should be --stationary--.
Column 8, Claim 13, line 32, "based the" should be --based on the--.

Signed and Sealed this

Twelfth Day of January, 2010

David J. Kappos
*Director of the United States Patent and Trademark Office*